US005698141A

United States Patent [19]

Kumar

[11] Patent Number: 5,698,141
[45] Date of Patent: Dec. 16, 1997

[54] PHOTOCHROMIC HETEROCYCLIC FUSED INDENONAPHTHOPYRANS

[75] Inventor: Anil Kumar, Pittsburgh, Pa.

[73] Assignee: PPG Industries, Inc., Pittsburgh, Pa.

[21] Appl. No.: 783,343

[22] Filed: Jan. 16, 1997

Related U.S. Application Data

[63] Continuation-in-part of Ser. No. 666,942, Jun. 17, 1996, abandoned.

[51] Int. Cl.$^6$ .......................... G02B 5/23; C07D 491/06; C07D 493/06; C07D 495/06
[52] U.S. Cl. .......................... 252/586; 524/84; 524/90; 524/110; 524/109; 548/417; 548/526; 549/41; 549/381; 544/141; 544/145; 544/150; 544/142; 546/197; 546/198; 546/276.7; 546/281.1; 546/282.7
[58] Field of Search .................... 549/41, 381; 548/417; 524/90, 84, 110; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/300 |
| 4,563,458 | 1/1986 | Widdig et al. | 514/253 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/586 |
| 4,931,221 | 6/1990 | Heller et al. | 252/586 |
| 5,066,818 | 11/1991 | Van Gemert et al. | 549/389 |
| 5,238,981 | 8/1993 | Knowles | 524/110 |
| 5,244,602 | 9/1993 | Van Gamert | 252/589 |
| 5,274,132 | 12/1993 | Van Gemert | 549/389 |
| 5,369,158 | 11/1994 | Knowles | 524/110 |
| 5,384,077 | 1/1995 | Knowles | 252/586 |
| 5,395,567 | 3/1995 | Van Gemert et al. | 252/586 |
| 5,405,958 | 4/1995 | Van Gemert et al. | 544/71 |
| 5,429,774 | 7/1995 | Kumar | 252/586 |
| 5,451,344 | 9/1995 | Knowles et al. | 252/586 |
| 5,458,814 | 10/1995 | Kumar et al. | 252/586 |
| 5,466,398 | 11/1995 | Van Gemert et al. | 252/586 |
| 5,514,817 | 5/1996 | Knowles | 549/384 |
| 5,552,090 | 9/1996 | Knowles | 252/586 |
| 5,578,252 | 11/1996 | Van Gemert et al. | 252/586 |
| 5,585,042 | 12/1996 | Van Gemert | 252/586 |

FOREIGN PATENT DOCUMENTS

| | | |
|---|---|---|
| 246114 | 11/1987 | European Pat. Off. . |
| 250193 | 12/1987 | European Pat. Off. . |
| 294056 | 12/1988 | European Pat. Off. . |
| 62-195383 | 8/1987 | Japan . |
| 02/69471 | 3/1990 | Japan . |
| 96/14596 | 5/1996 | WIPO . |

OTHER PUBLICATIONS

*Friedel–Crafts and Related Reactions*, George A. Olah, Interscience Publishers, vol. 3, Chap. XXXI, pp. 1–8, 1964.

"Regioselective Friedel Crafts Acylation of 1,2,3,4–Tetrahydroquinoline and Related Nitrogen Heterocycles: Effects of NH Protective Groups and Ring Size", Ishihara, Y., et al., J. Chem. Soc., Perkin Trans. 1, No. 24 pp. 3401–3406, Dec. 1992.

"1–Phenylnaphthalenes. Part IV. The Cyclisation of Methyl Hydrogen cis and trans–y–o–Methoxyphenyl—and Ethyl Hydrogen cis—and trans–y–p–Methoxyphenyl–y–phenylitaconate to the Corresponding 1–Phenylnaphthalenes", Baddar, F.G., et al., J. Chem. Soc., pp. 986–994, 1958.

"Behavior of a–Substituted Chalcones on Attempted Friedel–Crafts Arylation", Koelsch, C.F., The Journal of Organic Chemistry, vol. 267, pp. 2590–2592, 1961.

*The Chemistry of the Carbonyl Group*, Saul Patai, Editor, Interscience Publishers, Chapter 11, pp. 507–566, 1966.

Primary Examiner—Jose G. Dees
Assistant Examiner—Laura L. Stockton
Attorney, Agent, or Firm—Frank P. Mallak; Irwin M. Stein

[57] ABSTRACT

Described are novel photochromic heterocyclic fused indenonaphthopyran compounds having a substituted or unsubstituted heterocyclic ring fused to the g, h, i, n, o or p side of the indenonaphthopyran. These compounds may be represented by either of the following graphic formulae:

Also described are polymeric organic host materials that contain or that are coated with such compounds.

22 Claims, No Drawings

PHOTOCHROMIC HETEROCYCLIC FUSED INDENONAPHTHOPYRANS

CROSS REFERENCE TO RELATED APPLICATIONS

This application is a continuation-in-part of application Ser. No. 08/666,942, filed Jun. 17, 1996 now abandoned.

DESCRIPTION OF THE INVENTION

The present invention relates to certain novel naphthopyran compounds. More particularly, this invention relates to novel photochromic heterocyclic fused indenonaphthopyran compounds and to compositions and articles containing such novel indenonaphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions.

The present invention relates to novel indenonaphtho[1,2-b]pyran compounds having a substituted or unsubstituted heterocyclic ring, the 2,3 or 3,2 positions of which are fused to the g, h, i, n, o or p side of the indenonaphthopyran, and certain substituents at the 3-position of the pyran ring. These compounds have unexpectedly been found to demonstrate a bathochromic shift for the wavelength in the visible spectrum at which the maximum absorption of the activated (colored) form of the photochromic compound, i.e., the lambda max (Vis), occurs, thereby resulting in activated colors ranging from orange to blue/gray.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel indeno[2,1-f]naphtho[1,2-b]pyrans having activated colors ranging from orange to blue/gray may be prepared. These compounds may be described as indenonaphthopyrans having an unsubstituted, mono-substituted or di-substituted heterocyclic ring, the 2,3 or 3,2 positions of which are fused to the g, h, i, n, o or p sides of the indenonaphthopyran, and certain substituents at the 3 position of the pyran ring. Certain substituents may also be present at the number 5, 6, 7, 8, 9, 10, 11, 12, or 13 carbon atoms of the compounds. These indenonaphthopyran compounds may be represented by the following graphic formulae I and I' in which the letters a through p represent the sides of the compound, and the numbers 1 through 13 identify the ring atoms of the heterocyclic fused indenonaphthopyran. In the definitions of the substituents shown in formulae I and I', like symbols have the same meaning unless stated otherwise.

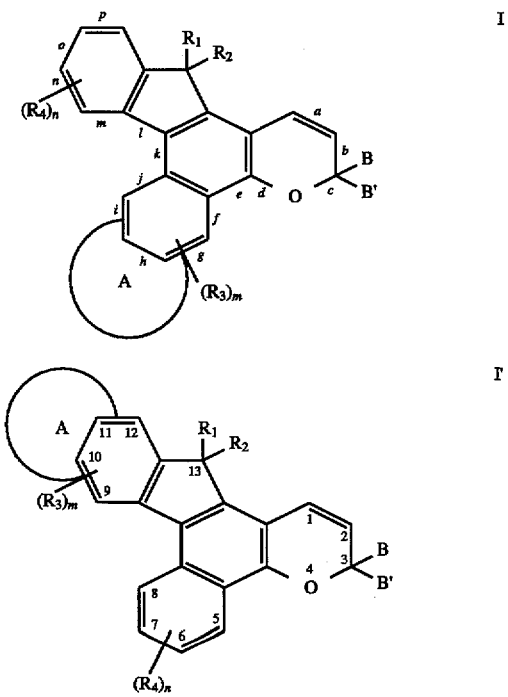

In graphic formulae I and I', A may be an unsubstituted, mono-substituted or di-substituted heterocyclic ring selected from the group consisting of benzothieno, benzofurano and indolo, the 2,3 or 3,2 positions of the heterocyclic ring being fused to the g, h, i, n, o or p side of the indenonaphthopyran. Each of the aforedescribed heterocyclic ring substituents may be $C_1$–$C_6$ alkyl, $C_5$–$C_7$ cycloalkyl, $C_1$–$C_6$ alkoxy, chloro or fluoro. Preferably, the heterocyclic ring A is unsubstituted or mono-substituted, and the heterocyclic ring substituents are $C_1$–$C_4$ alkyl or $C_1$–$C_4$ alkoxy. Most preferably, the heterocyclic ring A is unsubstituted or mono-substituted, the 2,3 or 3,2 position of the heterocyclic ring is fused to the g or p side of the indenonaphthopyran, and the heterocyclic ring substituents are $C_1$–$C_3$ alkyl or $C_1$–$C_3$ alkoxy.

$R_1$ and $R_2$, in graphic formulae I and I', may together form an oxo group, a spiro heterocyclic group having 2 oxygen atoms and from 3 to 6 carbon atoms including the spirocarbon atom, or $R_1$ and $R_2$ may each be selected from the group consisting of hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro and the group, —C(O)W, wherein each W is hydroxy, $C_1$–$C_6$ alkyl, $C_1$–$C_6$ alkoxy, phenyl, mono-substituted phenyl, amino, mono($C_1$–$C_6$)alkylamino or di($C_1$–$C_6$)alkylamino, or $R_1$ and $R_2$ may each be the group, —$OR_5$, wherein each $R_5$ is $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —$CH(R_6)X'$ wherein each $R_6$ is hydrogen or $C_1$–$C_3$ alkyl and each $X'$ is —CN, —$CF_3$, or —$COOR_7$, and each $R_7$ is hydrogen or $C_1$–$C_3$ alkyl, or each $R_5$ is the group, —C(O)Y, wherein each Y is hydrogen, $C_1$–$C_6$ alkyl, $C_1$–$C_6$ alkoxy, the unsubstituted, mono- or di-substituted aryl groups, phenyl and naphthyl, phenoxy, mono- or di-($C_1$–$C_6$) alkyl substituted phenoxy, mono- or di-($C_1$–$C_6$)alkoxy substituted phenoxy, amino, mono($C_1$–$C_6$)alkylamino, di($C_1$–$C_6$)alkylamino, phenylamino, mono- or di-($C_1$–$C_6$) alkyl substituted phenylamino or mono- or di-($C_1$–$C_6$) alkoxy substituted phenylamino, each of said aforedescribed phenyl, naphthyl and benzyl group substituents being $C_1$–$C_6$ alkyl or $C_1$–$C_6$ alkoxy.

Preferably, $R_1$ and $R_2$ are each selected from the group consisting of hydrogen, hydroxy, $C_1$–$C_4$ alkyl, $C_3$–$C_6$ cycloalkyl, chloro, fluoro and the group, —$OR_5$, wherein each $R_5$ is $C_1$–$C_3$ alkyl, phenyl($C_1$–$C_2$)alkyl, mono($C_1$–$C_3$) alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl, $C_1$–$C_3$ fluoroalkyl or the group, —$CH(R_6)X''$ wherein each $R_6$ is hydrogen or $C_1$–$C_2$ alkyl and each X is —CN or —$COOR_7$, and each $R_7$ is hydrogen or $C_1$–$C_2$ alkyl, or each $R_5$ is the group, —C(O)Y, wherein each Y is hydrogen, $C_1$–$C_3$ alkyl, $C_1$–$C_3$ alkoxy, phenyl, naphthyl, the mono-substituted aryl groups, phenyl and naphthyl, phenoxy, mono- or di-($C_1$–$C_3$)alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, and each of said aryl substituents being $C_1$–$C_3$ alkyl or $C_1$–$C_3$ alkoxy. Most preferably, $R_1$ and $R_2$ are each hydrogen, hydroxy, $C_1$–$C_4$ alkyl or the group, —$OR_5$, wherein each $R_5$ is $C_1$–$C_3$ alkyl.

In graphic formulae I and I', $R_3$ and $R_4$ may each be $C_1$–$C_6$ alkyl, $C_1$–$C_6$ alkoxy, chloro or fluoro, and m and n are each the integers 0, 1 or 2. Preferably, $R_3$ and $R_4$ are each $C_1$–$C_4$ alkyl, $C_1$–$C_4$ alkoxy, chloro or fluoro, and m and n are each the integers 0 or 1. Most preferably, $R_3$ and $R_4$ are each $C_1$–$C_3$ alkyl or $C_1$–$C_3$ alkoxy, and m and n are each the integers 0 or 1.

B and B' in graphic formulae I and I' may each be selected from the group consisting of: (i) the unsubstituted, mono-, di- and tri-substituted aryl groups, phenyl and naphthyl; (ii) the unsubstituted, mono- and di-substituted aromatic heterocyclic groups pyridyl, furanyl, benzofuran-2 -yl, benzofuran-3-yl, thienyl, benzothien-2-yl, benzothien-3-yl, dibenzofuranyl, dibenzothienyl, carbazolyl and fluorenyl, each of said aryl and aromatic heterocyclic substituents in parts (i) and (ii) being selected from the group consisting of hydroxy, aryl, mono($C_1$–$C_6$)alkoxyaryl, di($C_1$–$C_6$) alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$) alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di($C_1$–$C_6$)alkylaryl($C_1$–$C_6$)alkyl, mono- and di($C_1$–$C_6$) alkoxyaryl($C_1$–$C_6$)alkyl, mono- and di($C_1$–$C_6$)alkylaryl ($C_1$–$C_6$)alkoxy, mono- and di($C_1$–$C_6$)alkoxyaryl($C_1$–$C_6$) alkoxy, amino, mono($C_1$–$C_6$)alkylamino, di($C_1$–$C_6$) alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$) alkyl, acryloxy, methacryloxy, bromo, chloro and fluoro; (iii) the groups represented by the following graphic formulae:

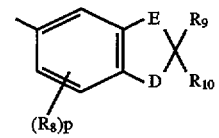

IIA

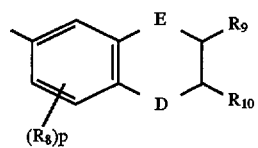

IIB wherein E may be carbon or oxygen and D may be oxygen or substituted nitrogen, provided that when D is substituted nitrogen, E is carbon, said nitrogen substituents being selected from the group consisting of hydrogen, $C_1$–$C_6$ alkyl and $C_2$–$C_6$ acyl; each $R_8$ is $C_1$–$C_6$ alkyl, $C_1$–$C_6$ alkoxy, hydroxy, bromo, chloro or fluoro; $R_9$ and $R_{10}$ are each hydrogen or $C_1$–$C_6$ alkyl; and p is the integer 0, 1 or 2; (iv) $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl ($C_3$–$C_6$)cycloalkyl, bromo($C_3$–$C_6$)cycloalkyl chloro($C_3$–$C_6$) cycloalkyl and fluoro($C_3$–$C_6$)cycloalkyl; and (v) the group represented by the following graphic formula:

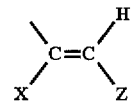

IIC wherein X in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, bromo, fluoro or chloro; or (vi) B and B' taken together form fluoren-9-ylidene, mono- or di-substituted fluoren-9-ylidene or form a member selected from the group consisting of saturated $C_3$–$C_{12}$ spiromonocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene and cyclododecylidene; saturated $C_7$–$C_{12}$ spiro-bicyclic hydrocarbon rings, e.g., bicyclo [2.2.1]heptylidene, i.e., norbornylidene, 1,7,7-trimethyl bicyclo[2.2.1]heptylidene, i.e., bornylidene, bicyclo[3.2.1]
octylidene, bicyclo[3.3.1]nonan-9-ylidene and bicyclo
[4.3.2]undecane and saturated $C_7$-$C_{12}$ spiro-tricyclic hydrocarbon rings, e.g., tricyclo[2.2.1.0$^{2,6}$]heptylidene and tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$-$C_4$ alkyl, $C_1$-$C_4$ alkoxy, bromo, fluoro and chloro.

More preferably, B and B' are each selected from the group consisting of: (i) phenyl, mono-substituted phenyl and di-substituted phenyl, preferably substituted in the meta and/or para positions; (ii) the unsubstituted, mono- and di-substituted aromatic heterocyclic groups furanyl, benzofuran-2-yl, thienyl, benzothien-2-yl, dibenzofuran-2-yl and dibenzothien-2-yl, each of said phenyl and aromatic heterocyclic substituents in (i) and (ii) being selected from the group consisting of hydroxy, aryl, aryloxy, aryl($C_1$-$C_3$) alkyl, amino, mono($C_1$-$C_3$)alkylamino, di($C_1$-$C_3$) alkylamino, N-($C_1$-$C_3$)alkylpiperazino, indolino, piperidino, morpholino, pyrryl, $C_1$-$C_3$ alkyl, $C_1$-$C_3$ bromoalkyl, $C_1$-$C_3$ chloroalkyl, $C_1$-$C_3$ fluoroalkyl, $C_1$-$C_3$ alkoxy, mono($C_1$-$C_3$)alkoxy($C_1$-$C_3$)alkyl, bromo, fluoro and chloro; (iii) the groups represented by the graphic formulae IIA and IIB, wherein E is carbon and D is oxygen, $R_8$ is $C_1$-$C_3$ alkyl or $C_1$-$C_3$ alkoxy, $R_9$ and $R_{10}$ are each hydrogen or $C_1$-$C_4$ alkyl; and p is the integer 0 or 1; (iv) $C_1$-$C_4$ alkyl; and (v) the group represented by the graphic formula IIC wherein X is hydrogen or methyl and Z is phenyl or mono-substituted phenyl, said phenyl substituent being selected from the group consisting of $C_1$-$C_3$ alkyl, $C_1$-$C_3$ alkoxy and fluoro; or (vi) B and B' taken together form fluoren-9-ylidene, mono-substituted fluoren-9-ylidene or a member selected from the group consisting of saturated $C_3$-$C_8$ spiro-monocyclic hydrocarbon rings, saturated $C_7$-$C_{10}$ spiro-bicyclic hydrocarbon rings and saturated $C_7$-$C_{10}$ spiro-tricyclic hydrocarbon rings, said fluoren-9-ylidene substituent being selected from the group consisting of $C_1$-$C_3$ alkyl, $C_1$-$C_3$ alkoxy, bromo, fluoro and chloro.

Most preferably, B and B' are each selected from the group consisting of (i) phenyl, mono- and di-substituted phenyl; (ii) the unsubstituted, mono- and di-substituted aromatic heterocyclic groups furanyl, benzofuran-2-yl, thienyl and benzothien-2-yl, each of said phenyl and aromatic heterocyclic substituents in (i) and (ii) being selected from the group consisting of hydroxy, $C_1$-$C_3$ alkyl, $C_1$-$C_3$ alkoxy, aryl, indolino, fluoro and chloro; (iii) the group represented by graphic formula IIA, wherein E is carbon and D is oxygen, $R_8$ is $C_1$-$C_3$ alkyl or $C_1$-$C_3$ alkoxy, $R_9$ and $R_{10}$ are each hydrogen or $C_1$-$C_3$ alkyl, and p is the integer 0 or 1; or (iv) B and B' taken together form fluoren-9-ylidene, adamantylidene, bornylidene, norbornylidene or bicyclo [3.3.1]nonan-9-ylidene.

Compounds represented by graphic formulae I and I' having the substituents $R_3$ and $R_4$, as described hereinbefore, may be prepared by the following described Reactions A through G. Compounds represented by graphic formula V or VA (as shown in Reactions A and B, respectively) are prepared by Friedel-Crafts methods Shown in Reaction A using an appropriately substituted or unsubstituted benzoyl chloride of graphic formula IV with a commercially available substituted or unsubstituted heterocyclic compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III (wherein X is oxygen, nitrogen or sulfur) and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V.

REACTION A

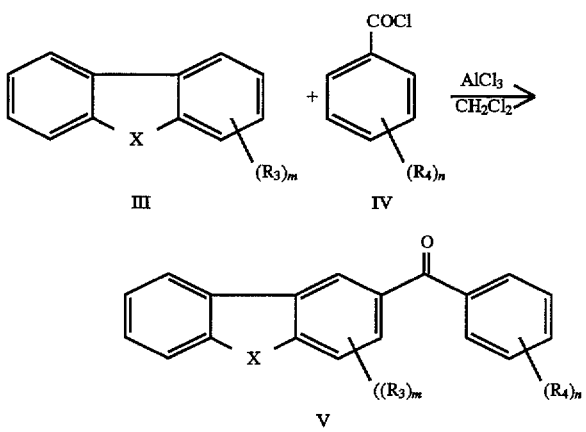

In Reaction B, the substituted or unsubstituted ketone represented by graphic formula VA is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

REACTION B

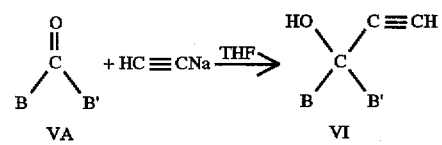

In Reaction C, the substituted or unsubstituted ketone represented by graphic formula V is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIII. The half ester (VIII) undergoes cyclodehydration in the presence of acetic anhydride to form the heterofused acetoxynaphthalenes represented by graphic formulae IXA and IXB. Compounds IXA and IXB were separated by crystallization, hydrolyzed in an aqueous alcoholic solution of base, such as sodium hydroxide, followed by treatment with aqueous hydrochloric acid ($H^+$) to form the carboxynaphthols represented by graphic formula XA or XB, respectively.

REACTION C

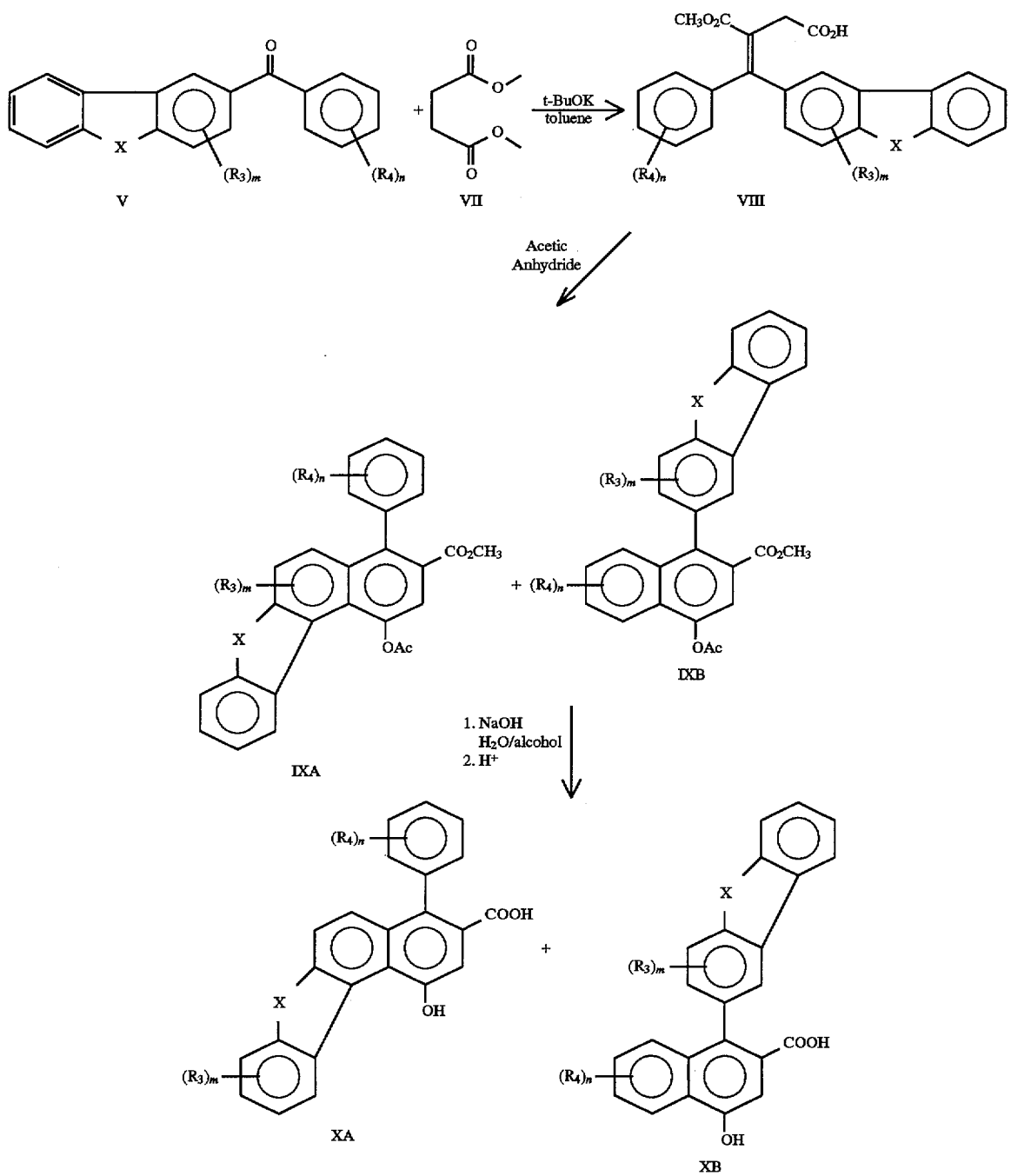

In Reaction D, the carboxynaphthols represented by graphic formulae XA and XB are cyclized by heating, e.g., from about 160 to about 220° C., in the presence of an acid, such as phosphoric acid, to form a hydroxy-substituted benz-fused fluorenone represented by graphic formulae XIA and XIB. See the article by F. G. Baddar et al, in the J. Chem. Soc., page 986, 1958. An alternate method of synthesizing the compound represented by graphic formula XIB is described by C. F. Koelsch in the Journal of Organic Chemistry, volume 26, page 2590, 1961.

Coupling of the compounds represented by graphic formulae XIA and XIB with propargyl alcohol represented by graphic formula VI in the presence of a catalytic amount of an acid, e.g., dodecylbenzene sulfonic acid (DBSA), results in the indeno-fused naphthopyran represented by graphic formulae IA and IB.

REACTION D
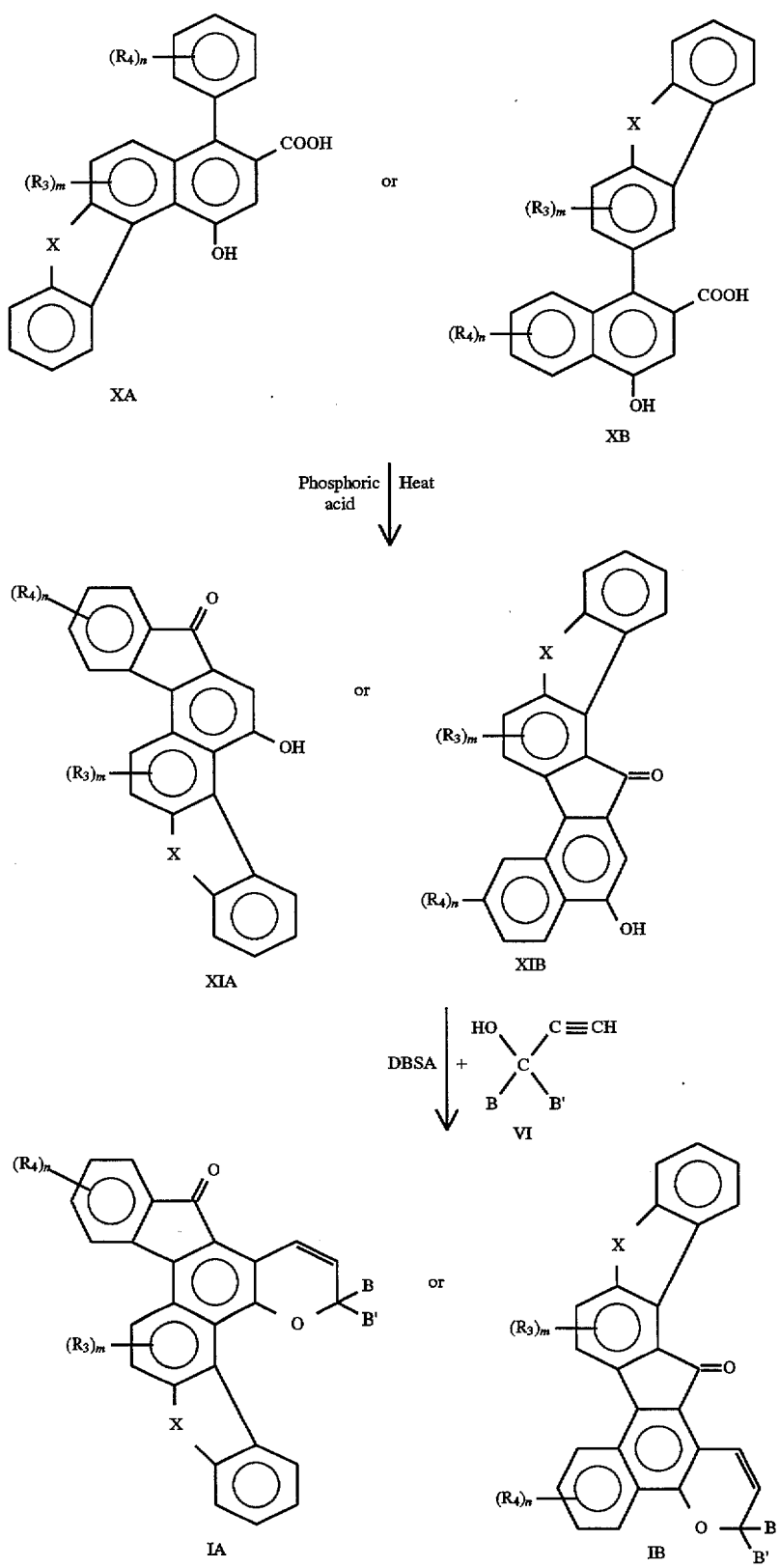
In Reaction E, the reduction of the compounds represented by graphic formulae XIA and XIB via the Wolff-Kishner reduction results in compounds represented by graphic formula XIIA and XIIB. Coupling of these compounds with propargyl alcohol represented by graphic formula VI results in the indeno-fused naphthopyrans represented by graphic formulae IC and ID. The replacement of the hydrogens shown on the indeno group in graphic formulae IC and ID by alkyl groups, e.g., $R_1$ and $R_2$, is accomplished by reaction of the compounds with trialkyl aluminum to produce the compound represented by graphic formulae IE and IF.

Compounds similar to the compounds represented by graphic formula IE and IF in which $R_1$ and $R_2$ are alkoxy instead of alkyl or $R_1$ and $R_2$ are taken together to form a spiro-heterocyclic group containing 2 oxygen atoms and 3 to 6 carbon atoms including the spirocarbon atom may be prepared by reacting the compounds represented by graphic formulae IA or IB with an alcohol or a diol, respectively, in the presence of a catalytic amount of acid.

REACTION E

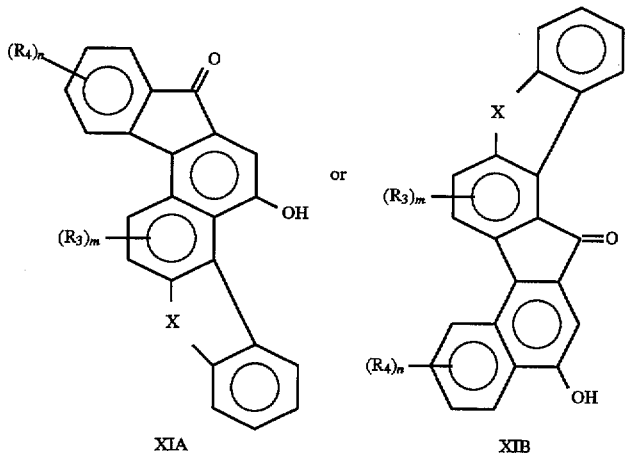

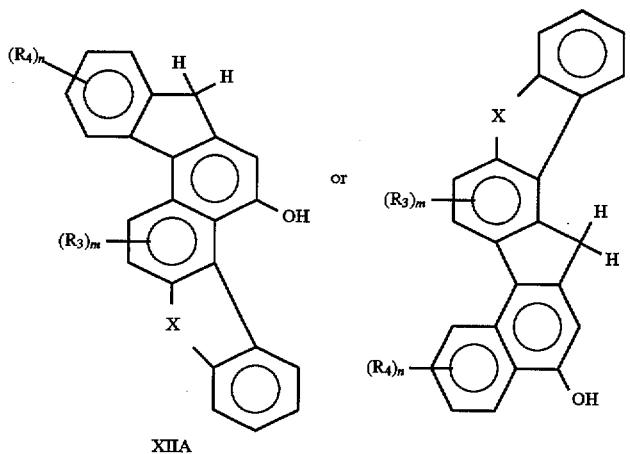

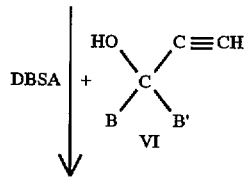

-continued
REACTION E

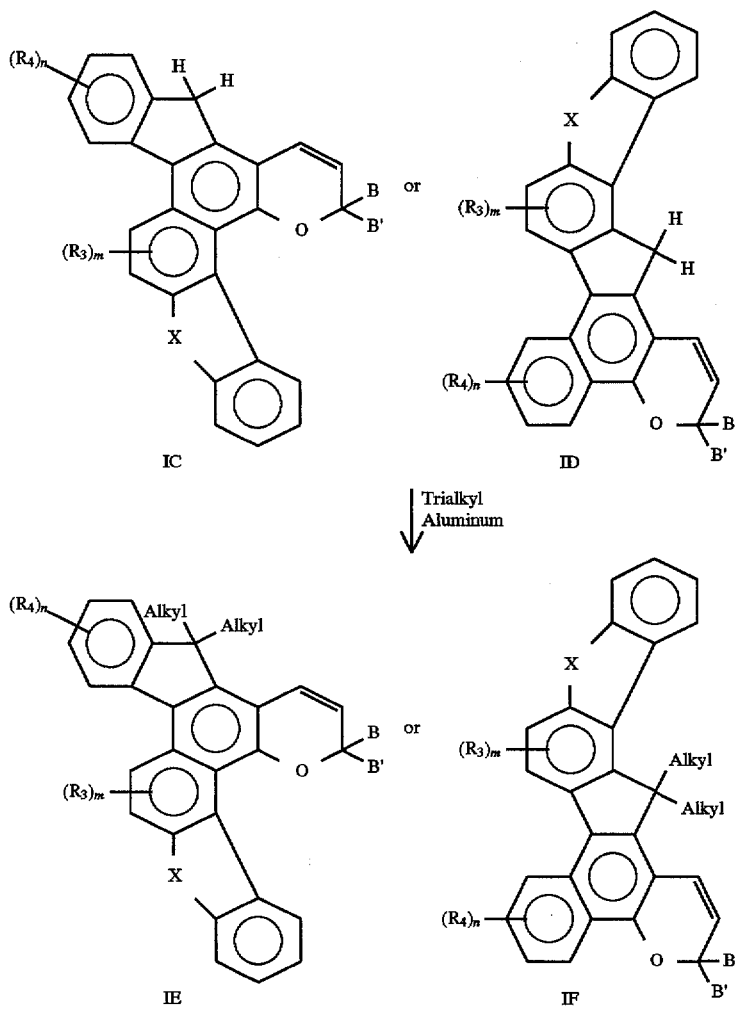

In Reactions F and G, further methods for preparing compounds represented by graphic formulae I and I' having a variety of $R_1$ and $R_2$ substituents are described. Starting with either of the compounds represented by graphic formula IA in Reaction F or IB in Reaction G, reduction with lithium aluminum hydride (LAH) results in the compound represented by graphic formula IG or IL, respectively. Other methods for reducing the carbonyl group are described in the text *The Chemistry of the Carbonyl Group*, Chapter 11, Saul Patai, Editor, 1966, Interscience Publishers.

The reaction of the compounds represented by graphic formulae IG or IL with an acyl chloride having the potential substituent R' results in compounds represented by graphic formula IJ or IN. Another pathway for incorporating different $R_1$ and $R_2$ substituents on the compounds represented by graphic formulae IA or IB is by reacting either of the compounds with a Grignard or lithium reagent having the potential substituent R to produce the compounds represented by graphic formula IH or IM. Subsequent reaction of the compounds represented by graphic formula IH or IM with an alcohol having the potential substituent R' in the presence of an acid such as hydrochloric acid results in the compound represented by graphic formula IK or IP.

REACTION F
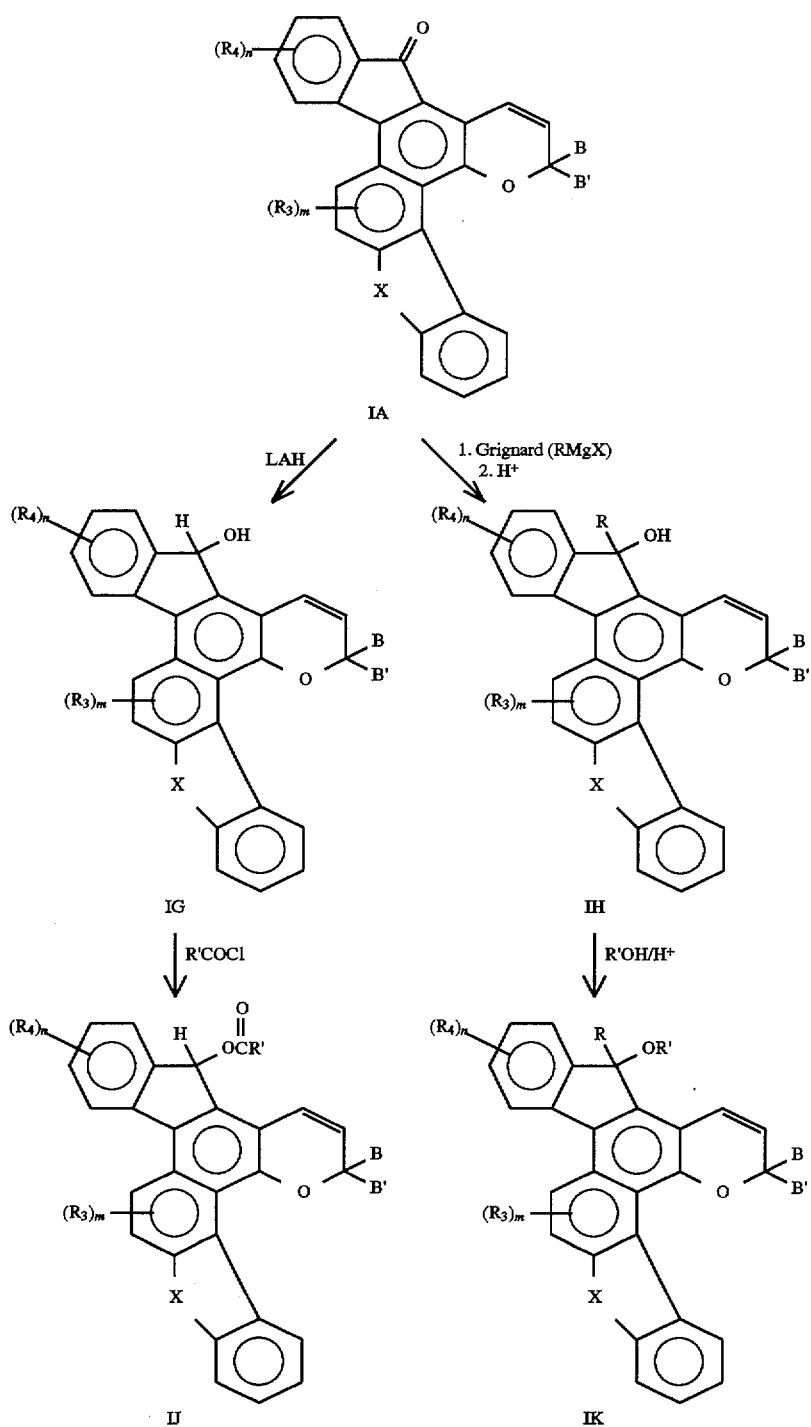

REACTION G

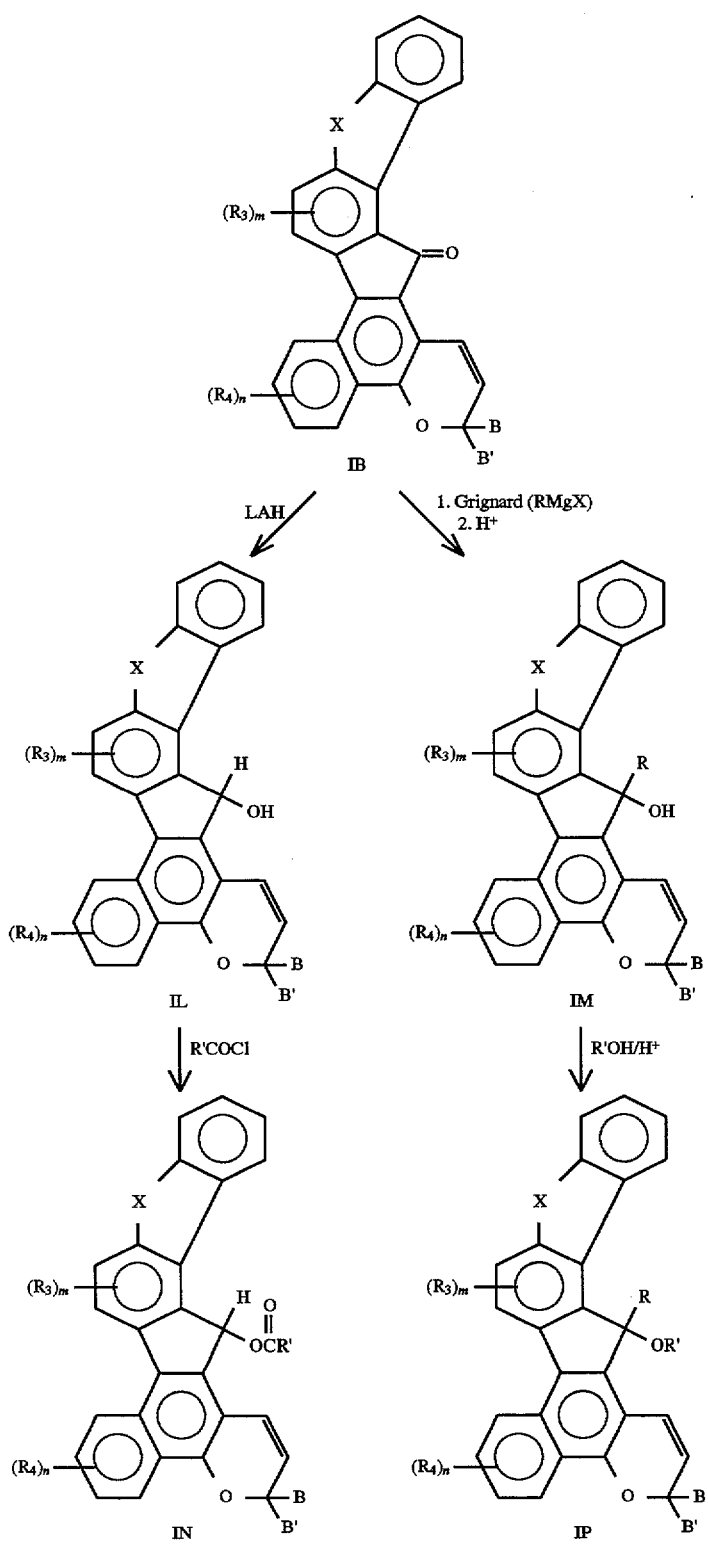

Compounds represented by graphic formula I, I', IA, IB, IC, ID, IE, IF, IG, IH, IJ, IK, IL, IM, IN and IP may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Heterocyclic fused indenonaphthopyrans represented by the aforedescribed graphic formulae exhibit color changes from colorless to colors ranging from orange to blue/gray.

Examples of contemplated indenonaphthopyran compounds within the scope of the invention include the following:

(a) 3,3-di(4-methoxyphenyl)-16-hydroxy-16-ethyl-16H-benzofuro[2',3':7,8]indeno[2',3':3,4]naphtho[1,2-b]pyran;

(b) 3,3-di(4-methoxyphenyl)-16-hydroxy-16H-benzofuro[2",3":6',7']indeno[3',2':4,3]naphtho[1,2-b]pyran; and (c) 3,3-di(4-methoxyphenyl)-16-hydroxy-16-ethyl-16H-benzofuro[2",3":6',7']indeno[3',2':4,3]naphtho[1,2-b]pyran.

It is contemplated that the organic photochromic indenonaphthopyrans of the present invention may be used alone, in combination with other indenonaphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than in the operating examples, or where otherwise indicated, all numbers expressing wavelengths, quantities of ingredients or reaction conditions used herein are to be understood as modified in all instances by the term "about".

Examples of complementary organic photochromic compounds include other naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines, and mixtures of such photochromic compounds.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form.

Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol methacrylate monomers and alkoxylated polyhydric alcohol acrylate monomers, such as ethoxylated trimethylol propane triacrylate monomers; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(oxyalkylene dimethacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic indenonaphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLE 1

Step 1

Dibenzofuran (40 grams, 0.23 mole) and benzoyl chloride (0.25 mole) were added to a reaction flask containing 500 milliliters (mL) of anhydrous methylene chloride and stirred at room temperature. Anhydrous aluminum chloride (0.30 mole) was added slowly to the mixture. The reaction mixture was stirred one hour and then poured into a 5 weight percent aqueous hydrochloric acid and ice mixture. The resulting mixture was stirred 15 minutes and extracted with methylene chloride. The organic layer was separated and washed first with 10 weight percent aqueous sodium hydroxide followed by distilled water. The organic layer was separated and dried over anhydrous magnesium sulfate. The methylene chloride solvent was removed under vacuum. The resulting oily product crystallized from hexane. The recovered product, 50 grams, was filtered and air dried. A nuclear magnetic resonance (NMR) spectrum showed the desired product to have a structure consistent with 2-benzoyl dibenzofuran.

Step 2

Potassium t-butoxide (35 grams, 0.31 mole) was slowly added to a reaction flask containing 600 mL of toluene, 2-benzoyl dibenzofuran (40 grams, 0.15 mole), and dimethyl succinate (30 grams, 0.20 mole) over a period of one-half hour. The resulting pasty mixture was refluxed for two hours, cooled, and about 400 mL of water was added and mixed well. The aqueous layer was separated, acidified with dilute hydrochloric acid, and extracted with 200 mL of toluene. The solvents, toluene and residual t-butanol, were removed on the rotary evaporator to produce a near quantitative yield of crude Stobbe half-ester: 4-(dibenzofur-2-yl) -4-phenyl-3-methoxycarbonyl-3-butenoic acid. This material was not purified further but was used directly in the next step.

Step 3

The crude half-ester from Step 2 was added to a reaction flask containing acetic anhydride (100 grams) and anhydrous sodium acetate (50 grams) and the mixture was refluxed for 4 hours. The mixture was cooled and the solvent was removed on a rotary evaporator. The resulting residue was dissolved in 200 mL of chloroform and stirred. Water (200 mL) was added followed by the slow addition of solid sodium carbonate until carbon dioxide evolution ceased.

The organic layer was separated and washed with water. The solvent, chloroform, was removed on a rotary evaporator to yield a viscous oil containing a mixture of 1-(dibenzofur-2-yl)-2-methoxycarbonyl-4-acetoxy-naphthalene and 1-acetoxy-3-methoxycarbonyl-4-phenyl-benzo[b]naphtho[1,2-d]furan. This material was not purified further but were used directly in the next step.

STEP 4

The oil containing 1-(dibenzofur-2-yl)-2-methoxycarbonyl-4-acetoxy-naphthalene and 1-acetoxy-3-methoxycarbonyl-4-phenyl-benzo[b]naphtho[1,2-d]furan from Step 3 was added to a reaction flask containing 100 mL of a 10 weight percent aqueous sodium hydroxide solution and 200 mL of methanol. The mixture was refluxed for 3 hours and cooled to room temperature to crystallize the desired product. The resulting crystals were suction filtered, washed with cold aqueous ethanol and dried. The recovered product, 15 grams, had a NMR spectrum consistent with 1-hydroxy-3-carboxyl-4-phenyl-benzo[b]naphtho[1,2-d]furan. The filtrate was poured into a beaker containing approximately one liter of cold (approx. 4° C.) dilute hydrochloric acid to crystallize the other desired product. About 20 grams of the resulting crystalline product was collected by vacuum filtration. A NMR spectrum showed the product to have a structure consistent with 1-(dibenzofur-2-yl)-4-hydroxy-2-naphthoic acid.

Step 5

1-Hydroxy-3-carboxyl-4-phenyl-benzo[b]naphtho[1,2-d]furan (10 grams) from Step 4 was added to a reaction flask (fitted with a Dean-Stark apparatus) containing 10 grams of p-toluene sulfonic acid and 50 mL of toluene. The resulting mixture was refluxed for five hours. During this time a deep red solid product formed. The mixture was cooled and 200 mL of water was added. The solid was broken up with a spatula, filtered, and washed successively with water, 5 weight percent aqueous sodium bicarbonate, and water. The recovered red colored product, 7 grams, had a NMR spectrum consistent with 5-hydroxy-7-oxo-7H-benzo[b]indeno[2',3':5,6]naphtho[1,2-d]furan.

Step 6

5-Hydroxy-7-oxo-7H-benzo[b]indeno[2',3':5,6]naphtho[1,2-d]furan (6 grams) from Step 5 was added to a reaction flask containing 50 mL of anhydrous tetrahydrofuran. The mixture was cooled in an ice bath and protected from moisture with a nitrogen pad while an excess of ethyl Grignard reagent was added to the reaction with stirring. After stirring an additional ten minutes, 50 mL of 5 weight percent aqueous hydrochloric acid was added and the organic layer was separated, washed with water and dried on anhydrous sodium sulfate. The solvent, tetrahydrofuran, was removed on a rotary evaporator. The addition of approximately 10 mL of diethyl ether to the residue caused the crystallization of desired product. This material, was filtered and dried to yield 4 grams of the desired product. An NMR spectrum showed the product to have a structure consistent with 5,7-dihydroxy-7-ethyl-7H-benzo[b]indeno[2',3':5,6]naphtho[1,2-d]furan.

Step 7

5,7-Dihydroxy-7-ethyl-7H-benzo[b]indeno[2',3':5,6]naphtho[1,2-d]furan (3 grams) from Step 6 was added to a reaction flask containing 1,1-di(4-methoxyphenyl)-2-propyn-1-ol, 2.5 grams, and 80 mL of toluene and the resulting mixture was stirred at room temperature. p-Toluene sulfonic acid, 100 mg, was added and stirring was continued for five hours. After the reaction mixture cooled to room temperature, it was filtered and the collected filtrate was washed three times with 10 weight percent aqueous sodium hydroxide. The solvent, toluene, was removed on a rotary evaporator. The oily crude product was column chromatographed on silica using a 1:1 mixture of hexane:chloroform as the elutant. The desired product, which crystallized from ether, was filtered and dried to yield 1.0 grams of a product having a melting range of 242°–244° C. An NMR spectrum showed the product to have a structure consistent with 3,3-di(4-methoxyphenyl)-16-hydroxy-16-ethyl-16H-benzofuro[2',3':7,8]indeno[2',3':3,4]naphtho[1,2-b]pyran.

EXAMPLE 2

Step 1

The process of Step 5 of Example 1 was followed except that 1-(dibenzofur-2-yl)-4-hydroxy-2-naphthoic acid from Step 4 of Example 1 was used in place of 1-hydroxy-3-carboxyl-4-phenyl-benzo[b]naphtho[1, 2-d]furan. A NMR spectrum showed the resulting product to have a structure consistent with 7-hydroxy-5-oxo-5H-benzo[b]naphtho [2',1':2,3 ]indeno [7, 6-d ]furan.

Step 2

7-Hydroxy-5-oxo-5H-benzo [b]naphtho [2',1':2,3]indeno [7,6-d]furan (10 grams) from Step 1 was added to a reaction flask containing 100 mL of anhydrous tetrahydrofuran and stirred. Small portions of lithium aluminum hydride were added to the stirred mixture until all of the red-orange color disappeared. The reaction mixture was stirred an additional 2 hours, quenched with a small amount of ethanol, and poured into 100 mL of 5 weight percent aqueous hydrochloric acid. The organic layer was separated, washed with water, filtered, and the solvent, diethyl ether, was removed on a rotary evaporator. A NMR spectrum showed the recovered product to have a structure consistent 5,7-dihydroxy-5H-benzo[b]naphtho[2',1':2,3]indeno[7,6-d]furan.

Step 3

The process of Step 7 of Example 1 was followed except that 5,7-dihydroxy-5H-benzo[b]-naphtho[2',1':2,3]indeno[7, 6-d]furan was used in place of 5,7-dihydroxy-7-ethyl-7H-benzo[b]indeno[2',3':5,6]naphtho[1,2-d]furan to produce 1.0 gram of a crystalline product that had a melting range of 240°–241° C. A NMR spectrum showed the product to have a structure consistent with 3,3-di(4-methoxyphenyl)-16-hydroxy-16H-benzofuro[2",3":6',7']indeno[3',2':4,3]naphtho[1,2-b]pyran.

EXAMPLE 3

The process of Example 2 was followed except that in Step 2 ethyl Grignard reagent was used in place of lithium aluminum hydride to produce 1.0 gram of a crystalline product that had a melting range of 257°–259° C. A NMR spectrum showed the product to have a structure consistent with 3,3-di(4 -methoxyphenyl)-16-hydroxy-16-ethyl-16H-benzofuro [2",3":6',7']indeno [3',2':4,3]naphtho [1,2-b] pyran

EXAMPLE 4

Part A

Testing was done with the photochromic indenonaphthopyrans of the previous Examples by incorporating them into polymeric samples by the following method. The quantity of indenonaphthopyran calculated to yield a 1.5 times $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The indenonaphthopyran was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven set to increase the temperature from 40° C. to 95° C. over a 5 hour interval, hold the temperature at 95° C. for 3 hours and then lower it to 60° C. for at least 2 hours before the end of the curing cycle. After the mold was opened, the polymer sheet was cut using a diamond blade saw into 2 inch (5.1 centimeters) test squares.

Part B

The photochromic test squares prepared in Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle normal to the square. After passing through the square, the light from the tungsten lamp was directed through a photopic filter attached to a detector. The photopic filter passes wavelengths such that the detector mimics the response of the human eye. The output signals from the detector(s) were processed by a radiometer.

Change in optical density (ΔOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula A OD=log(100/% Ta) where % Ta is the percent transmittance in the activated state and the logarithm is to the base 10.

The Δ OD/Min, which represents the sensitivity of the photochromic compound's response to UV light, was measured over the first five (5) seconds of UV exposure, then expressed on a per minute basis. The saturation optical density (OD) was taken under identical conditions as the Δ OD/Min, except UV exposure was continued for 20 minutes for the examples in Table 1. The lambda max reported in Table 1 is the wavelength in the visible spectrum at which the maximum absorption of the activated (colored) form of the photochromic compound in a diethylene glycol bis(allyl carbonate) composition occurs. The Bleach Rate (T ½) is the time interval in seconds for the absorbance of the activated form of the indenonaphthopyran in the test squares to reach one half the highest absorbance at room temperature (75° F., 23.9° C.) after removal of the source of activating light. Results for the Compounds of the Examples are tabulated in Table 1.

TABLE 1

| EXAMPLE COMPOUNDS | LAMBDA MAX (VISIBLE) | ΔOD/MIN SENSITIVITY | ΔOD@ SATU- RATION | Bleach (T1/2) |
|---|---|---|---|---|
| 1 | 597 nm | 0.25 | 0.12 | 23 |
| 2 | 574 nm | 0.19 | 0.26 | 70 |
| 3 | 580 nm | 0.20 | 0.21 | 48 |

The results of Table 1 show that a range of values for bleach rate, ΔOD at saturation, and sensitivity are obtained for the Example Compounds 1 through 3 of the present invention depending on the nature of the heterocyclic ring A, the side of fusion, and the substituents $R_1$, $R_2$, $R_3$, $R_4$, B and B'.

Although the present invention has been described with reference to the specific details of particular embodiments thereof, it is not intended that such details be regarded as limitations upon the scope of the invention except as and to the extent that they are included in the accompanying claims.

We claim:

1. An indenonaphthopyran compound represented by the following graphic formulae:

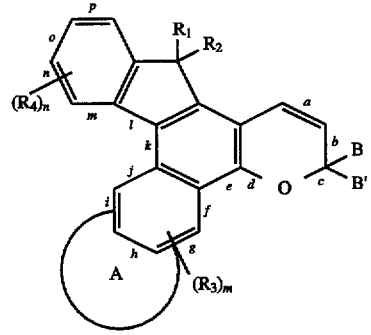

or

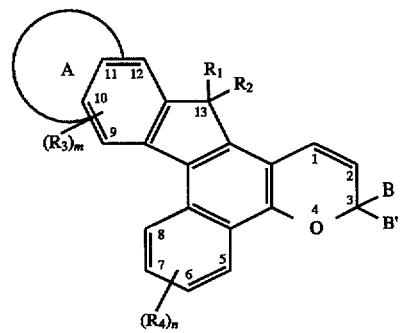

wherein, (a) A is an unsubstituted, mono-substituted or di-substituted heterocyclic ring selected from the group consisting of benzothieno, benzofurano and indolo, the 2,3 or 3,2 positions of said heterocyclic ring being fused to the g, h, i, n, o or p side of said indenonaphthopyran, said heterocyclic ring substituents being $C_1$–$C_6$ alkyl, $C_5$–$C_7$ cycloalkyl, $C_1$–$C_6$ alkoxy, chloro or fluoro;

(b) $R_1$ and $R_2$ together form an oxo group, a spiro heterocyclic group having 2 oxygen atoms and from 3 to 6 carbon atoms including the spirocarbon atom, or $R_1$ and $R_2$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro or the group, —C(O)W, wherein each W is hydroxy, $C_1$–$C_6$ alkyl, $C_1$–$C_6$ alkoxy, phenyl, mono-substituted phenyl, amino, mono($C_1$–$C_6$)alkylamino or di($C_1$–$C_6$) alkylamino, or $R_1$ and $R_2$ are each the group, —$OR_5$, wherein each $R_5$ is $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono ($C_1$–$C_4$)alkyl substituted $C_3$–$C_7$ cycloalkyl, $C_1$–$C_6$ chloroalkyl, $C_1$–$C_6$ fluoroalkyl, allyl, the group, —CH($R_6$)X' wherein each $R_6$ is hydrogen or $C_1$–$C_3$ alkyl, each X' is —CN, —CF3, or —$COOR_7$, and each $R_7$ is hydrogen or $C_1$–$C_3$ alkyl, or each $R_5$ is the group, —C(O)Y, wherein each Y is hydrogen, $C_1$–$C_6$ alkyl, $C_1$–$C_6$ alkoxy, an unsubstituted, mono- or di-substituted aryl group selected from phenyl and naphthyl, phenoxy, mono- or di-($C_1$–$C_6$)alkyl substituted phenoxy, mono- or di-($C_1$–$C_6$)alkoxy substituted phenoxy, amino, mono($C_1$–$C_6$)alkylamino, di($C_1$–$C_6$)alkylamino, phenylamino, mono- or di-($C_1$–$C_6$)alkyl substituted phenylamino or mono- or di-($C_1$–$C_6$)alkoxy substituted phenylamino, each of said phenyl, benzyl and aryl group substituents being $C_1$–$C_6$ alkyl or $C_1$–$C_6$ alkoxy;

(c) $R_3$ and $R_4$ are each $C_1$–$C_6$ alkyl, $C_1$–$C_6$ alkoxy, chloro or fluoro, and m and n are each the integers 0, 1 or 2; and (d) B and B' are each selected from the group consisting of:

(i) an unsubstituted, mono-, di- and tri-substituted aryl group selected from phenyl and naphthyl;

(ii) an unsubstituted, mono- and di-substituted aromatic heterocyclic group selected from pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and aromatic heterocyclic substituents in (d) (i) and (ii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$) alkyl, $C_3$–$C_7$ cycloalkyloxy($C_1$–$C_6$)alkoxy, aryl ($C_1$–$C_6$)alkyl, aryl($C_1$–$C_6$)alkoxy, aryloxy, aryloxy ($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono ($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro;

(iii) a group represented by one of the following graphic formulae:

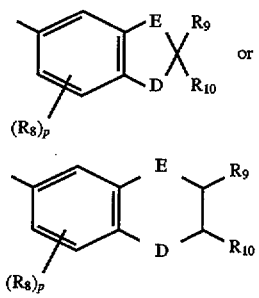

wherein E is carbon or oxygen and D is oxygen or substituted nitrogen, provided that when D is substituted nitrogen, E is carbon, said nitrogen substituents being selected from the group consisting of hydrogen, $C_1$–$C_6$ alkyl and $C_2$–$C_6$ acyl; each $R_8$ is $C_1$–$C_6$ alkyl, $C_1$–$C_6$ alkoxy, hydroxy, bromo, chloro or fluoro; $R_9$ and $R_{10}$ are each hydrogen or $C_1$–$C_6$ alkyl; and p is the integer 0, 1 or 2;

(iv) $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy ($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl ($C_3$–$C_6$)-cycloalkyl, bromo($C_3$–$C_6$)cycloalkyl, chloro($C_3$–$C_6$)cycloalkyl and fluoro($C_3$–$C_6$)cycloalkyl; and (v) a group represented by the following graphic formula:

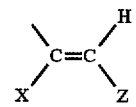

wherein X is hydrogen or $C_1$–$C_4$ alkyl and Z is selected from an unsubstituted, mono-, and di-substituted members of the group consisting of naphthyl, phenyl, furanyl and thienyl, each of said group substituents being $C_1$–$C_4$ alkyl, $C_1$–$C_4$ alkoxy, bromo, fluoro or chloro; or (vi) B and B' taken together form fluoren-9-ylidene, mono- or di-substituted fluoren-9-ylidene or a member selected from the group consisting of a saturated $C_3$–$C_{12}$ spiro-monocyclic hydrocarbon ring, a saturated $C_7$–$C_{12}$ spiro-bicyclic hydrocarbon ring and a saturated $C_7$–$C_{12}$ spiro-tricyclic hydrocarbon ring, each of said fluoren-9-ylidene substituents being selected from the group consisting of $C_1$–$C_4$ alkyl, $C_1$–$C_4$ alkoxy, bromo, fluoro and chloro.

2. The indenonaphthopyran of claim 1 wherein:

(a) the heterocyclic ring A is unsubstituted or mono-substituted, and said heterocyclic ring substituents are $C_1$–$C_4$ alkyl or $C_1$–$C_4$ alkoxy;

(b) $R_1$ and $R_2$ are each selected from the group consisting of hydrogen, hydroxy, $C_1$–$C_4$ alkyl, $C_3$–$C_6$ cycloalkyl, chloro, fluoro and the group, —$OR_5$, wherein $R_5$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl, $C_1$–$C_3$ fluoroalkyl or the group, —CH($R_6$)X', wherein $R_6$ is hydrogen or $C_1$–$C_2$ alkyl and X' is —CN or —$COOR_7$, and $R_7$ is hydrogen or $C_1$–$C_2$ alkyl, or $R_5$ is the group, —C(O)Y, wherein Y is hydrogen, $C_1$–$C_3$ alkyl, $C_1$–$C_3$ alkoxy, phenyl, naphthyl, a mono-substituted aryl group selected from phenyl and naphthyl, phenoxy, mono- or di-($C_1$–$C_3$) alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, and each of said aryl substituents being $C_1$–$C_3$ alkyl or $C_1$–$C_3$ alkoxy;

(c) $R_3$ and $R_4$ are each $C_1$–$C_4$ alkyl, $C_1$–$C_4$ alkoxy, chloro or fluoro, and m and n are each the integers 0 or 1; and (d) B and B' are each selected from the group consisting of:
  (i) phenyl, mono-substituted phenyl and di-substituted phenyl;
  (ii) an unsubstituted, mono-substituted and di-substituted aromatic heterocyclic group selected from furanyl, benzofuran-2-yl, thienyl, benzothien-2-yl, dibenzofuran-2-yl, and dibenzothien-2-yl, each of said phenyl and aromatic heterocyclic substituents in (d) (i) and (ii) being selected from the group consisting of hydroxy, aryl, aryloxy, aryl($C_1$–$C_3$) alkyl, amino, mono($C_1$–$C_3$)alkylamino, di($C_1$–$C_3$) alkylamino, N-($C_1$–$C_3$)alkylpiperazino, indolino, piperidino, morpholino, pyrryl, $C_1$–$C_3$ alkyl, $C_1$–$C_3$ bromoalkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, bromo, fluoro and chloro;
  (iii) a group represented by one of the following graphic formulae:

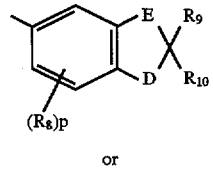

or

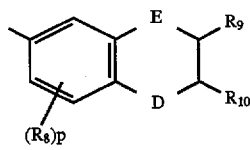

wherein E is carbon and D is oxygen, $R_8$ is $C_1$–$C_3$ alkyl or $C_1$–$C_3$ alkoxy, $R_9$ and $R_{10}$ are each hydrogen or $C_1$–$C_4$ alkyl; and p is the integer 0 or 1; and
  (iv) $C_1$–$C_4$ alkyl; and
  (v) a group represented by the following graphic formula:

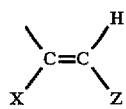

wherein X is hydrogen or methyl and Z is phenyl or mono-substituted phenyl, said phenyl substituent being selected from the group consisting of $C_1$–$C_3$ alkyl, $C_1$–$C_3$ alkoxy and fluoro; or
  (vi) B and B' taken together form a fluoren-9-ylidene, mono-substituted fluoren-9-ylidene or a member selected from the group consisting of a saturated $C_3$–$C_8$ spiro-monocyclic hydrocarbon ring, a saturated $C_7$–$C_{10}$ spiro-bicyclic hydrocarbon ring and a saturated $C_7$–$C_{10}$ spiro-tricyclic hydrocarbon ring, said fluoren-9-xylidene substituent being selected from the group consisting of $C_1$–$C_3$ alkyl, $C_1$–$C_3$ alkoxy, bromo, fluoro and chloro.

3. The indenonaphthopyran of claim 2 wherein:
  (a) the heterocyclic ring A is unsubstituted or mono-substituted, the 2,3 or 3,2 position of said heterocyclic ring being fused to the g or p side of said indenonaphthopyran, and said heterocyclic ring substituents being $C_1$–$C_3$ alkyl or $C_1$–$C_3$ alkoxy;
  (b) $R_1$ and $R_2$ are each hydrogen, hydroxy, $C_1$–$C_4$ alkyl or the group, —$OR_5$, wherein $R_5$ is $C_1$–$C_3$ alkyl;
  (c) $R_3$ and $R_4$ are each $C_1$–$C_3$ alkyl or $C_1$–$C_3$ alkoxy, and m and n are each the integers 0 or 1; and
  (d) B and B' are each selected from the group consisting of:
    (i) phenyl, mono-substituted and di-substituted phenyl;
    (ii) an unsubstituted, mono-, and di-substituted aromatic heterocyclic group selected from furanyl, benzofuran-2-yl, thienyl and benzothien-2-yl, each of said phenyl and aromatic heterocyclic substituents in (d) (i) and (ii) being selected from the group consisting of hydroxy, $C_1$–$C_3$ alkyl, $C_1$–$C_3$ alkoxy, aryl, indolino, fluoro and chloro; and
    (iii) a group represented by the following graphic formula:

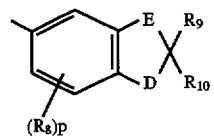

wherein E is carbon and D is oxygen, $R_8$ is $C_1$–$C_3$ alkyl or $C_1$–$C_3$ alkoxy, $R_9$ and $R_{10}$ are each hydrogen or $C_1$–$C_3$ alkyl, and p is the integer 0 or 1; or
    (iv) B and B' taken together form fluoren-9-ylidene, adamantylidene, bornylidene, norbornylidene or bicyclo(3.3.1)nonan-9-ylidene.

4. An indenonaphthopyran compound selected from the group consisting of:
  (a) 3,3-di(4-methoxyphenyl)-16-hydroxy-16-ethyl-16H-benzofuro[2',3':7,8]indeno[2',3':3,4]naphtho[1,2-b]pyran;
  (b) 3,3-di(4-methoxyphenyl)-16-hydroxy-16H-benzofuro[2",3":6',7']indeno[3',2':4,3]naphtho[1,2-b]pyran; and
  (c) 3,3-di(4-methoxyphenyl)-16-hydroxy-16-ethyl-16H-benzofuro[2",3":6',7']indeno[3',2':4,3]naphtho[1,2-b]pyran.

5. A photochromic article comprising a polymeric organic host material and a photochromic amount of the indenonaphthopyran compound of claim 1.

6. The photochromic article of claim 5 wherein the polymeric organic host material is selected from the group consisting of poly($C_1$–$C_{12}$ alkyl methacrylates), poly (oxyalkylene dimethacrylates), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol methacrylate monomers, alkoxylated polyhydric alcohol acrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly (ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

8. The photochromic article of claim 7 wherein the photochromic compound is present in an amount of from about 0.05 to 1.0 milligram per square centimeter of organic host material surface to which the photochromic substance (s) is incorporated or applied.

9. The photochromic article of claim 8 wherein the article is a lens.

10. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers and a photochromic amount of the naphthopyran compound of claim 2.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the indenonaphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host material, and a photochromic amount of each of (a) at least one indenonaphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly (oxyalkylene dimethacrylates), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro (indoline)benzopyrans, spiro(indoline)naphthopyrans, spiro (indoline)quinopyrans, spiro(indoline)pyrans, spiro (indoline)naphthoxazines, spiro(indoline) pyridobenzoxazines, spiro(benzindoline) pyridobenzoxazines, spiro(benzindoline)naphthoxazines, spiro(indoline)benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance (s) is incorporated or applied.

20. The photochromic article of claim 19 wherein the article is a lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one indenonaphthopyran compound of claim 2, and (b) at least one other organic photochromic compound having at least one activated absorption maxima within the range of between about 400 and 700 nanometers.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one indenonaphthopyran compound of claim 3, and (b) at least one other organic photochromic compound having at least one activated absorption maxima within the range of between about 400 and 700 nanometers.

* * * * *